(12) United States Patent
Suetsugu et al.

(10) Patent No.: US 6,607,116 B2
(45) Date of Patent: Aug. 19, 2003

(54) METHOD AND APPARATUS FOR ESTIMATING QUALITY OF LEAD-FREE SOLDER MATERIAL AND PROCESS AND SYSTEM FOR FLOW SOLDERING

(75) Inventors: Kenichiro Suetsugu, Nishinomiya (JP); Shunji Hibino, Hirakata (JP); Yukio Maeda, Hirakata (JP); Shoshi Kabashima, Hirakata (JP); Mikiya Nakata, Suita (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/874,038

(22) Filed: Jun. 6, 2001

(65) Prior Publication Data

US 2002/0000460 A1 Jan. 3, 2002

(30) Foreign Application Priority Data

Jun. 6, 2000 (JP) ........................................ 2000-168903
Jun. 6, 2000 (JP) ........................................ 2000-168904

(51) Int. Cl.[7] ............................ B23K 31/02; B23K 37/00
(52) U.S. Cl. ........................... 228/102; 228/8; 228/37; 228/103; 228/260
(58) Field of Search ............................ 228/102, 103, 228/8, 9, 256, 260, 33, 37

(56) References Cited

U.S. PATENT DOCUMENTS

| | | | |
|---|---|---|---|
| 4,224,744 A | * | 9/1980 | Siegel et al. |
| 5,248,199 A | | 9/1993 | Reading |
| 5,346,306 A | | 9/1994 | Reading et al. |
| 5,527,628 A | * | 6/1996 | Anderson et al. |
| 5,657,924 A | | 8/1997 | Wandke et al. |
| 6,231,691 B1 | * | 5/2001 | Anderson et al. |

FOREIGN PATENT DOCUMENTS

| | | |
|---|---|---|
| EP | 0 858 859 | 8/1998 |
| EP | 1162021 A1 * | 12/2001 |
| WO | 95/33199 | 12/1995 |

OTHER PUBLICATIONS

US 2002/0117539A1 Ito et al. (Aug. 29, 2002).*
US 2002/0000460A1 Suetsugu et al. (Jan. 3, 2002).*
Ramsey, T.H. "Use of Differential Thermal Analysis in Controlling Behavior of Solder–Glass Seals in Ceramic Packages", Solid State Technology, vol. 15, No. 1 (1972), pp. 29–33, 43.
Lau, J.H., et al. "TMA, DMA, DSC, and TGA of Lead Free Solders", 1998 Proceedings of the 48th Electronic Components and Technology Conference, Seattle, WA May 25–28, 1998, pp. 1339–1344.
Patent Abstracts of Japan, vol. 2000, No. 20 of JP 2001–058286 (Mar. 2001).
G. Chaumarat, "Analyse thermique: Contrôle-Qualité des structures collées", CETIM–Informations, No. 126, pp. 61–66, Feb. 1992.

* cited by examiner

*Primary Examiner*—Tom Dunn
*Assistant Examiner*—Kiley Stoner
(74) *Attorney, Agent, or Firm*—Wenderoth, Lind & Ponack, L.L.P.

(57) ABSTRACT

There is provided a method which can conveniently estimate a quality of a lead-free solder material used for a flow soldering process. In the present invention, a differential thermal analysis curve of a sample of the lead-free solder material is obtained by utilizing a differential thermal analysis method, and thereby a quality of the lead-free solder material used for a flow soldering process is estimated based on the obtained differential thermal analysis curve.

19 Claims, 4 Drawing Sheets

METHOD AND APPARATUS FOR ESTIMATING QUALITY OF LEAD-FREE SOLDER MATERIAL AND PROCESS AND SYSTEM FOR FLOW SOLDERING

CROSS-REFERENCE TO RELATED APPLICATIONS

The present application claims a priority under 35 U.S.C. §119 to Japanese Patent Applications No. 2000-168903, filed on Jun. 6, 2000, entitled "METHOD FOR ESTIMATING QUALITY OF LEAD-FREE SOLDER MATERIAL AND PROCESS AND SYSTEM FOR FLOW SOLDERING" and No. 2000-168904, filed on Jun. 6, 2000, entitled "APPARATUS FOR ESTIMATING QUALITY OF LEAD-FREE SOLDER MATERIAL". The contents of these applications are incorporated herein by the reference in their entirety.

BACKGROUND OF THE INVENTION

1. Field of the Invention

The present invention relates to a method and an apparatus for estimating a quality of a lead-free solder material which is used for a flow soldering process of, for example, mounting an electronic component on a board (or a substrate). The present invention also relates to a process and a system for flow soldering which are combined with such method and/or apparatus for estimating the quality of the lead-free solder material.

2. Description of Related Art

For production of an electronic circuit board which is to be incorporated in an electronic device, electronic components are conventionally mounted on a board (or a substrate) such as a printed circuit board using a so-called "flow soldering" process (which is also called as a "wave soldering" process). A general flow soldering process will be described below.

Prior to soldering, there is prepared a board on which at least one electronic component is located by inserting a lead(s) (e.g. an electrode(s)) drawn from the electronic component into a through hole perforating through the board. It is noted that a land made of copper foil or the like is formed to cover a wall of the through hole as well as regions surrounding the through hole on an upside and an underside of the board, respectively, and this land is connected to a wiring pattern(s) on the upside of the board. In addition, regions on the upside and the underside of the board excluding the lands are coated with a solder resist to repel a molten solder material.

Next, while the board is mechanically conveyed at an approximately constant velocity in a flow soldering apparatus, a solder material which is preheated in a solder bath to melt is supplied in the form of a solder wave(s) to the board from the underside of the board. At this stage, the molten solder material which is supplied as described above rises from the underside of the board and through an annular space between the wall of the through hole and the lead inserted to the through hole from the upside of the board by means of a capillary phenomenon with wetting, and then the solder material solidifies by drop of temperature to form a connecting portion made of the solder material. On the other hand, most of the solder material which is supplied as described above is not provided into the annular space and returns to the solder bath by the gravity while it remains in the molten state (i.e. before solidifying), and it is supplied again in the form of the solder wave.

In this way, the connecting portion made of the solder material is formed to electrically and mechanically connect the lead of the electronic component with the land formed on the board, and thereby an electronic circuit board is produced.

For such an electronic circuit board, a solder material of an Sn—Pb system which includes Sn and Pb as major components has been generally used hitherto. However, it is beginning to use a so-called "lead-free" solder material (i.e. a solder material which substantially comprises no lead element), especially an Sn based solder material on an industrial scale as the alternative to the lead-including solder material since a lead element in the Sn—Pb based solder material may cause environmental pollution if it is wasted through wrongful disposal.

When electronic circuit boards are produced on an industrial scale continuously for a long duration by using the lead free solder material (which is also simply referred to as "a solder material" hereinafter) in the flow soldering process as described above, there may arise problems of a higher defective fraction which is derived from so-called "bridges", insufficient solder wetting of the through hole and the lead ("hu-nure" in Japanese) or the like, and of lower reliability characteristics which are derived from a so-called "lift-off" phenomenon, a lowered connection strength or the like compared with a case using the lead-including solder material. Thus, in a case using the lead-free solder material, flow soldering is practically conducted while at least a part of the solder material in a solder bath is periodically replaced with a fresh solder material in order to avoid such problems.

SUMMARY OF THE INVENTION

We have found that the problems as described above are originated in a change of a composition of the solder material since the molten solder material is contacted with the board in the form of the wave(s), and the most of the solder material is recovered in the solder bath, followed by being recycled in the flow soldering process, which will be described in detail as below.

In the flow soldering process, the board which is contacted with the molten solder material in the form of the wave includes various members, and materials used for some of those members (e.g. a wiring pattern formed on the underside of the board, a plating metal and a base metal of a lead of an electric component) may elute into the solder material as contaminants or impurities (or additional components) of the solder material when the members contact with the molten solder material. An Sn—Pb based material is still prevailingly used as a plating material for a lead of an electronic component currently, so that it is inevitable for Pb to accumulate as a contaminant in the solder material. In addition, an Sn—Bi based material is also used as a lead-free plating material in recent years, and Bi possibly melts and accumulates as a contaminant in the solder material in this case. Furthermore, a Zn-containing alloy material is used as a base material for a lead, and Zn possibly melts and accumulates as a contaminant in the solder material if a plating material covering such base material melts. In addition to these elements, Cu which is used as a wiring pattern material may become a contaminant (or an additional component). A part of the solder material supplied in the form of the wave which has not been used for connection with the electronic component is returned to and recovered in the solder bath while containing such contaminants. Thus recovered solder material is again supplied in the form of the wave(s). By repeating the above supplying and returning, the contaminants accumulate gradually in the molten solder material located in the solder bath, so that a composition of the solder material shifts from an initial composition.

It has been found that such shift of composition may cause the problems of the higher defective fraction of products and the lower reliability characteristics described above in the case using the lead-free solder material, although such shift hardly causes any problem in the case using the Sn—Pb based solder material. For example, from results of tensile tests as acceleration tests of a solder material which is prepared by adding Pb as an impurity to a lead-free solder material, it has been found that a destructive mode of a connection changes from that of a connection made by the original lead-free solder material. Moreover, according to results of tests as to lift-off occurrence rate of a solder material which is prepared by adding Cu or Bi to an Sn—Cu based solder material (e.g. a material which consists substantially of about 0.7% by weight of Cu and the balance of Sn), it has been found that the lift-off generation rate rises with the increase in an amount of the added Cu or Bi. Moreover, it has turned out that a rate of defective products having bridges rapidly increases when a content of Cu exceeds a certain point in the Sn—Cu based solder material.

Therefore, in order to prevent the fact that the higher defective fraction and the lower reliability characteristics are brought about remarkably, it is necessary to check (or analyze) a composition of the solder material in the solder bath periodically, and to control the composition. In order to check whether the composition of the solder material is maintained appropriately or not, it is generally conceivable to obtain a sample of the solder material from the solder bath and to analyze this sample by means of an analyzing instrument such as an atomic absorption spectroscopy or an X ray analysis instrument. However, such way of analysis has other problems in that these instruments requires complicated operations and take a long period, for example several days, although it can perform analysis of the composition with a high accuracy.

Then, the present invention has been made in order to realize that a quality of a lead-free solder material used for a flow soldering process can be estimated conveniently.

We have found that a quality of a lead-free solder material used for a flow soldering process can be estimated with ease based on a differential thermal analysis curve (or a differential thermal analysis thermogram) which is obtained as to the lead-free solder material, and have completed the present invention.

According to the present invention, there is provided a method for estimating a quality of a lead-free solder material which is used for a flow soldering process, which method comprises obtaining a differential thermal analysis curve of a sample of the lead-free solder material relatively to a reference material by utilizing a differential thermal analysis method so as to estimate the quality of the lead-free solder material based on the differential thermal analysis curve, and also provided a quality estimation apparatus for such method.

For example, it is conceivable to compare, in order to estimate the quality of the solder material, the differential thermal analysis curve of the sample of the lead-free solder material in question with other differential thermal analysis curve of a sample of a lead-free solder material having a criterial composition. As the later sample of the lead-free solder material having the criterial composition, a sample of a solder material which has, for example, an initial composition or a critical composition can be used. The comparison as described will be explained in detail later.

Alternatively, it is conceivable to compare, in order to estimate the quality of the solder material, a characteristic value derived from the differential thermal analysis curve of the sample of the lead-free solder material in question with other characteristic value as a threshold value derived from other differential thermal analysis curve of a sample of a lead-free solder material having a criterial composition, preferably a critical composition which is obtained according to a predetermined manner. For example, the predetermined manner is selecting a peak value, a liquidus point or a solidus point of the differential thermal analysis curve of each sample as the characteristic value. This comparison as described will be explained in detail later.

We have found that it is possible to estimate whether a solder material has a composition shifted from a predetermined composition or not, i.e. to estimate the quality of the solder material, based on the differential thermal analysis curve obtained as to the solder material, which will be described below in detail. According to the quality estimation method and/or the quality estimation apparatus of the present invention, it is possible to estimate the quality of the solder material by a simple operation in a short period, and therefore the quality of the solder material can be estimated by an ordinary operator immediately. Moreover, the quality estimation apparatus of the present invention has advantages in that it can be installed in a smaller space because of its compact size and can minimize an influence of a production cost of an electronic circuit board because of its lower price even though the quality estimation is conducted routinely, when compared with a conventional analyzing instruments.

Furthermore, according to the present invention, there is also provided a flow soldering process and a flow soldering system in which the quality estimation method and/or the quality estimation apparatus of the present invention is utilized. In addition to the advantages similar to those of the quality estimation method and/or the quality estimation apparatus of the present invention, the flow soldering process and the flow soldering system of the present invention have advantages in that it can estimate the quality of the solder material with ease at a site where the flow soldering is carried out, and that the quality of the solder material can be controlled routinely.

BRIEF DESCRIPTION OF THE DRAWINGS

A more complete appreciation of the invention and a number of the attendant advantages therefrom will become readily apparent with reference to the following detailed description, particularly when considered in conjunction with the accompanying drawings, in which.

The following numerals denote the following elements: 1 . . . furnace; 2 . . . heater; 3 and 4 . . . cell; 5, 6 and 7 . . . thermocouple; 8 . . . lid; 10 . . . sensor; 11 . . . A/D converter; 12 . . . processor; 13 . . . input unit; 14 . . . display unit; 15 . . . heater controller; 16, 17, and 18 . . . measurement unit; 20 . . . control device; and 30 . . . quality estimation apparatus.

DETAILED DESCRIPTION OF THE INVENTION

As described above, we have found that a quality of a lead-free solder material used for a flow soldering process is estimated with ease by utilizing a differential thermal analysis method, and have completed the present invention. The present invention is founded on the fact that a thermal property, and particularly a differential thermal analysis curve, of a solder material changes or shifts when the solder material having a predetermined composition (or an initial or fresh composition) is mixed or contaminated with an additional component(s), and the present invention resides in estimating the quality of the solder material utilizing this fact.

The differential thermal analysis method is a well-known analysis method, and it generally means a method for analyzing a thermal property of a sample wherein a temperature difference between the sample and a reference material (or standard material) is measured as a differential thermal analysis curve while the sample and the reference material are heated under the same condition. For example, a differential thermal analysis curve of a sample can be obtained by locating a sample and a reference material in an electric furnace, and then heating (or heating and cooling by the case) the sample and the reference material under substantially the same condition, and meantime measuring a temperature difference between the sample and the reference material directly, or measuring temperatures of the sample and the reference material respectively followed by calculating the temperature difference between these temperatures.

Figure 1A:
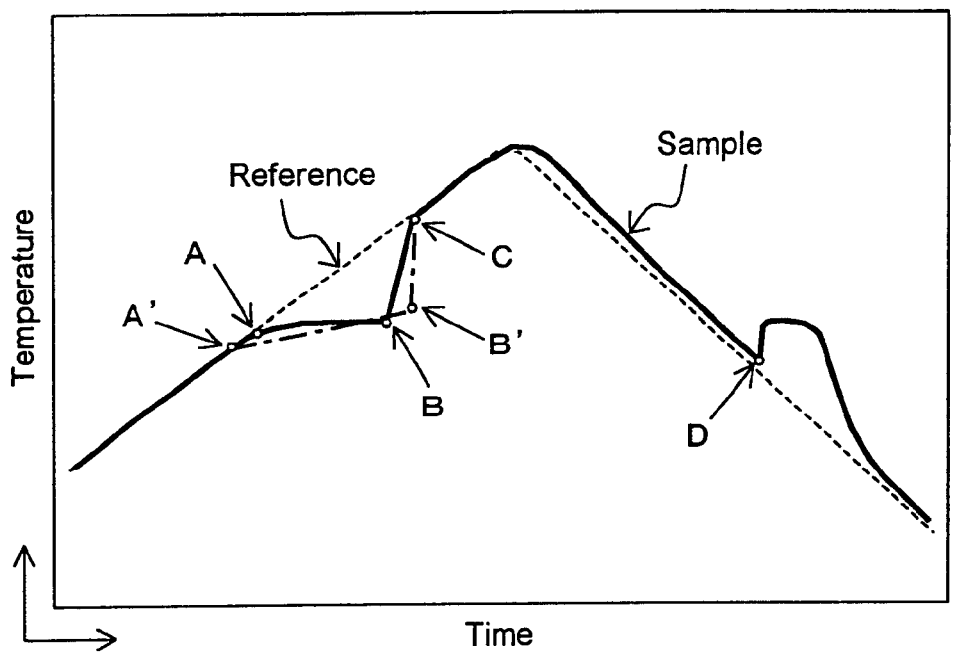
FIG. 1A shows a graph which schematically shows temperature changes of a solder material and a reference material, which are measured by means of a quality estimation apparatus of the present invention.
Figure 1B:
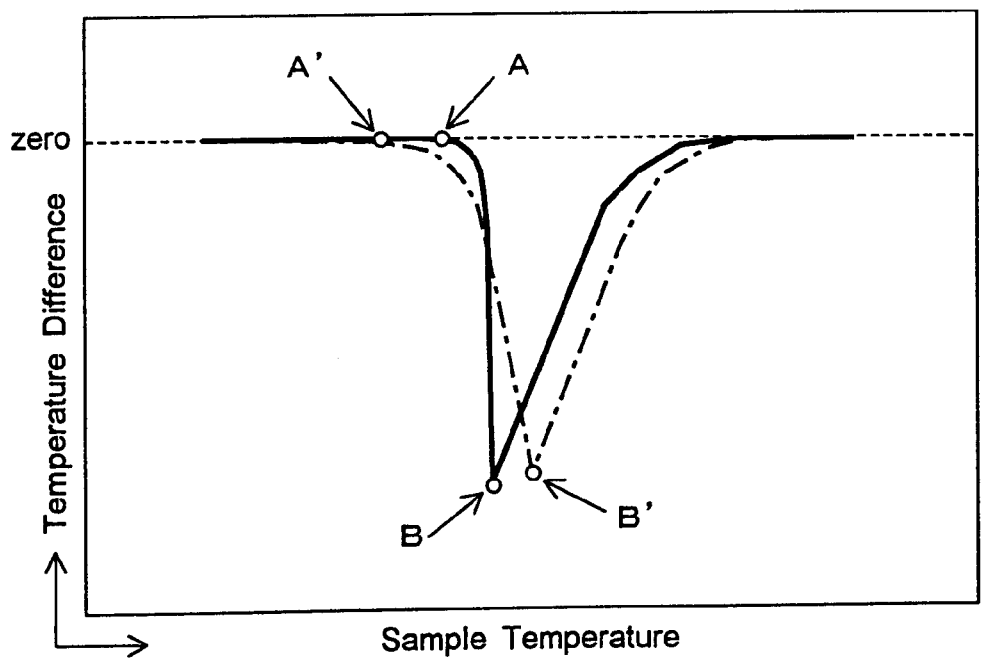
FIG. 1B shows a graph which schematically shows a part of a differential thermal analysis curve of the solder material, which is obtained from a graph of FIG. 1A.

It will be described below with reference to drawings that the quality of the solder material can be estimated by using such differential thermal analysis method. FIG. 1A shows a graph which schematically shows temperature changes of a solder material and of a reference material, wherein the temperatures are measured by means of a quality estimation apparatus of the present invention which can be utilized for conducting the quality estimation method of the present invention. FIG. 1B shows a graph which schematically shows a part of a differential thermal analysis curve of the solder material which is obtained from the graph of FIG. 1A. It is noted that the quality estimation apparatus will be described later.

At first, a sample of the solder material (which is also merely referred to as a "sample" hereinafter) and the reference material (which is also merely referred to as a "reference" hereinafter) are set in the quality estimation apparatus. It is noted that the sample consists of the solder material having a certain composition, for example, an eutectic composition. On the other hand, the reference material consists of a thermally stable material which can avoid its phase change within a temperature range in which the temperature measurement is carried out. Then, each temperature change with time of the sample and the reference is measured while the sample and the reference are heated and thereafter cooled under the same condition by heating and thereafter cooling containers which contain the sample and the reference respectively, for example, by heating and thereafter cooling a furnace in which the containers are placed. In this way, a temperature curve (also referred as to a temperature change with time) of the sample (shown partly as the solid line in FIG. 1A) as well as a temperature curve of the reference (shown partly as the doted line in FIG. 1A) are obtained. The temperature range for the measurement is set to extends across a melting point or a melting range (if having a partly molten condition over a certain temperature range) of the solder material in question.

With reference to the left hand side of the graph in FIG. 1A, although the sample shows substantially the same temperature change as that of the reference material during the initial stage of heating, the temperature change of the sample is nearly flat from Point A to Point B followed by rapidly rising from Point B to Point C, and the sample shows the same temperature change again as that of the reference material during the subsequent heating. This can be explained as follows: During the initial stage of heating, the temperature of the sample gradually increases with time similarly to that of the reference material. During this stage, the sample is in its solid phase condition. However, the sample starts to melt when the temperature of the sample reaches Point A, and thereafter a temperature of the sample does not increase since a quantity of heat subsequently added to the sample is used as a heat for liquefaction. The liquefaction of the sample proceeds while keeping the temperature at Point A until the liquefaction of the sample is completed at Point B. Thereafter, a quantity of heat added to the sample is used for the temperature increase of the sample, so that the temperature of the liquefied sample is increased and approaches that of the reference material. On the other hand, the temperature of the reference material gradually increases with time during the heating as shown in Fig. A since it is maintained in single phase, for example a solid phase. The temperature of Point A at which the sample starts melting is also referred to as a "solidus point", and the temperature of Point B at which the sample completes melting is also referred to as a "liquidus point", herein.

Furthermore, when the liquefied sample is subsequently subjected to cooling as shown in the right hand side of the graph in FIG. 1A, the sample shows substantially or almost the same temperature change with time as that of the reference material during the initial stage of cooling. However, the temperature of the sample steeply rise at Point D followed by keeping almost constant, and then falls gradually and follows the reference material. This can be explained as follows: The liquefied sample once becomes in a state of supercooling, and then begins to solidify and releases heat of solidification at Point D. As a result, the sample temperature is rapidly increase at Point D to a temperature which is almost same as the temperature between the Points A and B where the sample is in a state of mixed phases of solid and liquid. The solidification of the sample proceeds and ends at that temperature. After the sample completes the solidification, the temperature of the sample starts to fall again by releasing heat to its circumference atmosphere and approaches the temperature of the reference material.

If a solder material which shows the temperature change with time as described above is changed in its composition by being contaminated with an additional component(s) (or an element(s)) which may be the same as and/or different from the components or elements of the solder material, the temperature change with time (i.e. temperature curve) will be changed, for example, from the curve shown as a solid line (from Point A to Point C through Point B) into the curve shown as an alternate long and short dash line (from Point A' to Point C through Point B') as shown in FIG. 1A. Such change of the temperature curve appears also as a change of a liquidus point and/or a solidus point. For example, Point A as the solidus point is shifted to Point A' on the lower temperature side, and Point B as the liquidus point is shifted to Point B' on the higher temperature side as shown in FIG. 1A. Which shift of the solidus point and the liquidus point takes place, or whether both shifts take place, depends on the composition of the solder material which has been resulted from the contamination (or addition) of the added component into the initial solder material. For example, there are two types of the components cause the shift with respect to a certain solder material, one type causes the shift of the solidus point, and the other type causes the shift of the liquidus point, and hereinafter, these two types of components are referred to as a "low melting point component" and a "high melting point component", respectively. Moreover, when both of the low melting point component and the high melting point component are added to a solder material, these shifts may compositely take place. With respect to the Sn—Cu based solder material, for example, Pb, Bi and Zn are the low melting point components and Cu is the high melting point components.

Such change of the temperature curve of the sample of the solder material as described above also appears as a change of a differential thermal analysis curve obtained by subtracting the temperature curve of the reference material from the temperature curve of the sample (or a (plotted) curve of "Temperature Difference", which is obtained by subtracting the temperature curve of the reference material from that of the sample, vs. "Sample Temperature" as shown in FIG. 1B). The differential thermal analysis curve of the solder material shown in FIG. 1B as the solid line changes into the alternate long and short dash line shown in FIG. 1B by the contamination with the additional component into the solder material. For example, if an additional component is mixed into a solder material which has an eutectic composition, it can be seen in FIG. 1B that a differential thermal analysis curve changes from the solid line to the alternate long and short dash line, so that a sample temperature at which a "Temperature Difference" begins to appear (i.e. a temperature where "Temperature Difference" is just away from zero so that a negative "Temperature Difference" begins to appear) changes from Point A to Point A', and/or a sample temperature which corresponds to a peak of the differential thermal analysis curve (i.e. a temperature which gives a maximum negative Temperature Difference) changes from Point B to Point B'. Such changes correspond to the shifts as mentioned above.

Although the changes (or shifts) in the temperature curve of the sample and in the differential thermal analysis curve of the sample on heating are described as above, it is also understandable for those skilled in the art that changes (or shifts) similar to the above occurs on cooling.

Furthermore, it is clear that the shift (or deviation) of the composition of the solder material (i.e. the quality change of the solder material) can be estimated based on the differential thermal analysis curve not only in the case where an initial (or original) solder material has an eutectic composition as described above, but also in the case where an initial (or original) solder material has the other composition since the change (or shift) of the differential thermal analysis curve depends on the composition of the solder material.

We have found that estimation regarding whether the solder material has a composition shifted from a predetermined (or initial) composition or not, i.e. the estimation of the quality of the solder material, can be conducted with a simple operation based on change in the differential thermal analysis curve as described above. As a result, there are realized a novel quality estimation method which can estimate the quality of the lead-free solder material with a simple operation, and an apparatus for such method. Additionally, there are also realized a flow soldering process and a flow soldering system utilizing such quality estimation method and/or such apparatus.

Therefore, in one aspect of the present invention, there is provided a quality estimation method for estimating a quality of a lead-free solder material which is used for a flow soldering process, which method comprises obtaining a differential thermal analysis curve of a sample of the lead-free solder material relatively to a reference material by utilizing a differential thermal analysis method to estimate the quality of the lead-free solder material based on the differential thermal analysis curve. According to this method, the quality of the solder material, specifically, a shift of a composition of the solder material from a certain composition can be readily estimated. The quality estimation method of the present invention can be conducted by a simpler operation and in a shorter period compared with a conventional analytical method of the solder material. For example, it can be conducted in less than one hour, preferably in less than thirty minutes. Such method of the present invention has advantages in that it can estimate the quality of the solder material with ease in situ where flow soldering is carried out, and that the quality of the solder material can be controlled routinely.

More particularly, such quality estimation method of the present invention can be conducted by comparing the differential thermal analysis curve of the sample of the lead-free solder material in question with other differential thermal analysis curve of a sample of a lead-free solder material having a criterial composition in view of each configuration of the differential thermal analysis curves. As the later sample of the lead-free solder material having the criterial composition, a sample of a solder material which has, for example, an initial composition or a critical composition can be used. It is noted that the initial composition means a composition which is not contaminated with an additional component(s), and the critical composition means a composition which is made by mixing the additional component(s) of a maximally tolerant amount with the solder material having the initial composition. The comparison as described will be explained in detail later.

It is also noted that a "predetermined composition" or a "certain composition" is used herein to refer to a composition (or a composition range) which is to be maintained as to the solder material and/or a composition which is not contaminated or mixed with an additional component(s), for example, an initial or ideal composition of the solder material as described above. As the solder material having the certain composition, a lead-free solder material generally known may be used. For example, as the solder material having said "certain composition", there are, but not limited to, a solder material containing 0.5 to 1.0% by weight of Cu and the balance of Sn; a solder material containing 0.5 to 1.0% by weight of Cu, 0 to 0.5% by weight (excluding zero %) of Ag and the balance of Sn; a solder material containing 2.5 to 4.0% by weight of Ag, 0.5 to 1.0% by weight of Cu and the balance of Sn; and a solder material which is made by adding other component(s) such as Ni, P or the like to any one of those materials as above.

For obtaining the differential thermal analysis curve of the sample of the lead-free solder material relatively to the reference material, a substance which is thermally stable in the measuring temperature range is used as the reference material as generally used. For example, alumina, iron, a circumferential gas (i.e. making a container (or a cell) for the reference material empty) or the like may be used as the reference material. However, the present invention is not limited to this embodiments, and other material which can not avoid its phase change within the measuring temperature range can also be used as the reference material. For example, the solder material having the predetermined composition is preferably used as the reference material. In this case, the shift of the sample from the certain composition can be estimated directly with a higher accuracy.

In the quality estimation method of the present invention, the differential thermal analysis curve of the sample of the solder material is generally obtained relatively to the reference material as described above. However, the present invention is not limited to the above embodiments, and the differential thermal analysis curve of the sample of the solder material is also obtained by using, as the reference material, a surrounding (or a surrounding thermal atmosphere) of the sample.

In one embodiment, the estimation method of the present invention further comprises obtaining a characteristic value of a phase change of the sample of the lead-free solder material based on the differential thermal analysis curve to estimate the quality of the lead-free solder material. For example, such differential thermal analysis curve can be obtained, but not limited to, in the form of data by measuring temperatures of the sample and the reference material with time and digitize thus measured temperatures so as to obtain (digital) data for the temperature curves of the sample and of the reference material, respectively, followed by data processing to subtract the data of the temperature curve of the reference material from corresponding data of the temperature curve of the sample.

On the other hand, the characteristic value of the phase change can be any value as long as it changes depending on the composition of the solder material, and it can be selected properly by those skilled in the art. For example, a sample temperature at which the temperature difference between the sample and the reference begins to occur as to the differential thermal analysis curve (or a temperature of the solidus point such as a temperature at Point A or A' in FIG. 1B), or a sample temperature at which the temperature difference reaches maximum (or a temperature of the liquidus point such as a temperature at Point B or B' in FIG. 1B) on heating can be used as the characteristic value of the phase change. Instead of these values, it is possible to use other characteristic value which will change according to the composition of the solder material on heating. Alternatively, it is also possible to use a peak temperature value of the differential thermal analysis curve on cooling as the characteristic value of the phase change. These exemplary characteristic values of the phase change can be obtained by processing data of the differential thermal analysis curve as described in the above example in a suitable arithmetic manner.

In another embodiment, the quality estimation method of the present invention further comprises comparing the characteristic value of the phase change of the sample of the lead-free solder material with a predetermined threshold value to obtain a comparative result between these values. It is noted that the "comparative result" is a result through comparing the characteristic value of the phase change with the threshold value. For example, the comparative result is obtained by calculating a difference between these values (e.g. [characteristic value of phase change]–[threshold value]) or a ratio of these values (e.g. [characteristic value of phase change]/[threshold value]).

The threshold value as above can be predetermined based on a characteristic value of a phase change of a solder material which is made by addition of at least one component as an additional component(s), which is possibly mixed into the lead-free solder material, to the solder material having the predetermined composition in such an amount that such addition makes a quality of the lead-free solder material unacceptable as to its soldering properties. For example, the at least one component (e.g. a contaminant element) as the additional component(s) is selected from the group consisting of Cu, Pb, Ag, Bi and Zn, and the component are preferably Pb and/or Cu. More specifically, in the case where a lead-free solder is an Sn—Cu based material which contains 0.5 to 1.0% by weight of Cu and the balance of Sn, an Sn—Cu—Ag based material which contains 0.5 to 1.0% by weight of Cu, 0 to 0.5% by weight (excluding zero %) of Ag and the balance of Sn, or an Sn—Ag—Cu based material which contains 2.5 to 4.0% by weight of Ag, 0.5 to 1.0% by weight of Cu and the balance of Sn, the threshold value is preferably determined based on a characteristic value of a phase change of a solder material which is made by adding at least one element selected from the group consisting of Cu, Pb, Ag, and Bi to such lead-free solder. The characteristic value of the phase change for determining the threshold value can be obtained by subjecting the solder material mixed with the additional component(s) to the differential thermal analysis so as to obtain the differential thermal analysis curve of this material, and processing data of the differential thermal analysis curve in a manner as described above.

One example of procedures for determining the threshold value will be explained below. Firstly, a solder material is prepared by intentionally adding an element (or a material) which possibly melts and mixes into a flow (or a wave) of a molten lead-free solder material in a flow soldering process as an additional component to the solder material having the predetermined (or initial) composition. As such added element, an element (or a material) for members of a circuit board such as a plating metal member and a base metal member for a lead as well as a wiring pattern formed on a backside of the board is exemplified. For the case where electronic components are connected to a board by using thus prepared solder material, a dependency of reliability characteristics such as a connecting strength and a generation rate of the lift-off phenomenon as well as a dependency of product quality (or defective fraction) such as generation of bridges on an addition amount of the additional element are examined. Based on the results of such examination, a tolerance limit of the addition amount of the additional element (or material) is derived. Then, a material which is made by mixing the additional element of the tolerance limit amount with the solder material having the predetermined (or initial) composition (i.e. a material having the critical composition) is subjected to the differential thermal analysis, so that data of a differential thermal analysis curve as to such material is obtained. Thus obtained data is processed to derive a characteristic value of the phase change, especially a sample temperature at which temperature difference between a sample of the material and a reference material on the differential thermal analysis curve begins to appear on heating (i.e. a temperature of the solidus point such as that of Point A' in FIG. 1B) or a sample temperature at which the temperature difference reaches maximum on heating (i.e. a temperature of the liquidus point such as that of Point B' in FIG. 1B). The characteristic value of the phase change which is derived as described above can be used as the threshold value.

It should be noted that the procedures for determining the threshold value as described above is an exemplary one, and it can be modified in various ways. For instance, when a plurality of the elements (or materials) can be expected to be additionally mixed into the solder material having the predetermined composition, the threshold value may be determined by using added amounts of such materials as individual parameters. Furthermore, a plurality of threshold values as to one or each element can be set in order to estimated the change of the quality of the solder material in grades.

It is possible to estimate the quality of the solder material based on the comparative result as described above which is obtained by comparing the characteristic value of the sample of the solder material in question with the threshold value which has been predetermined as described above. More particularly, if the characteristic value of the sample of the solder material approaches the threshold value and finally exceeds it during a series of the comparisons, it can be considered that an amount of the additional component exceeding the tolerance limit is mixed in the solder material. In this way, the quality of the solder material can be estimated based on the comparative result. Examples of procedures for comparing the characteristic value with the threshold value will be explained as below, but the present invention is not limited to these examples.

In one example, a difference of a characteristic value relative to the threshold value approaches zero and thereafter changes its sign to be inverted when an amount of an added element as a contaminant which is mixed into the solder material is increased. In the case where a characteristic value of a initial solder material having a predetermined composition is larger than a threshold value, the difference (=[characteristic value]–[threshold value]) initially has a plus (positive) sign, and approaches zero with progress of accumulation of the contaminant when a flow soldering operation is prolonged, and finally becomes to have a minus (negative) sign when the characteristic value is smaller than the threshold value in due course. On the contrary, in the case where the characteristic value of the initial solder material having a predetermined composition is smaller than the threshold value, it will be understandable that an explanation contrary to the above is applicable.

In another example, a ratio of a characteristic value to a threshold value approaches 1 and thereafter is across 1 when an amount of an added element as a contaminant which is mixed into the solder material is increased. In the case where a characteristic value of a initial solder material having a predetermined composition is larger than a threshold value, the ratio (=[characteristic value]/[threshold value]) is initially larger than 1, and approaches 1 with progress of accumulation of the contaminant when a flow soldering operation is prolonged, and finally becomes to be smaller than 1 when the characteristic value is smaller than the threshold value in due course. On the contrary, in the case where the characteristic value of the initial solder material having a predetermined composition is smaller than the threshold value, it will be understandable that an explanation contrary to the above is applicable.

Based on the comparative result as described above, it is possible to judge whether an operation of flow soldering in a flow soldering process is to be continued or stopped. When the comparative result shows that the characteristic value of the phase change of the solder material sample does not exceed the threshold value, it is judged that the flow soldering can be continued using the current solder material since the quality thereof is sufficient. On the other hand, when the comparative result shows that the characteristic value of the phase change of the solder material sample exceeds the threshold value, it is judged that the flow soldering should not be continued using the solder material as it is since the quality thereof is insufficient, and that it is desirable to take a suitable action which makes the quality of the solder material used for flow soldering sufficiently high because increase of the defective product fraction and decrease of the reliability characteristics of the produced circuit board may be caused if the flow soldering is continuously conducted using such insufficient solder material.

In one embodiment of the present invention, an alarm is provided with a lamp, a sound or the like in order to inform an operator of the insufficient quality of the solder material depending on the comparative result obtained by comparing the characteristic value of the phase change of the sample of the solder material with the threshold value. In addition to, or in place of it, a flow soldering apparatus is controlled by a feedback controlling system depending on the comparative result in order to renew at least a part of the solder material in the solder bath of the flow soldering apparatus for making the quality of the solder material sufficiently high or to stop the operation of the flow soldering apparatus.

In another aspect of the present invention, there is provided a quality estimation apparatus for estimating a quality of a lead-free solder material which is used for a flow soldering process, wherein the quality of the lead-free solder material is estimated based on a differential thermal analysis curve of a sample of the lead-free solder material relative to a reference material obtained by a differential thermal analysis method. Such quality estimation apparatus is preferably used for conducting the quality estimation method of the present invention as described above and has similar effects to those achieved by the above mentioned quality estimation method. That is, the quality of the solder material, more specifically, shift of the composition of the solder material from a predetermined composition can be readily estimated by using the quality estimation apparatus of the present invention, and it can be operated with a simpler operation in a shorter period, for example, in less than one hour, and preferably in less than thirty minutes compared with an analyzing instrument which has been conventionally used for analyzing the composition of the solder material. Furthermore, such apparatus of the present invention has advantages in that it becomes possible to simply estimate the quality of the solder material in situ where the flow soldering is carried out, and that the quality of the solder material can be controlled routinely.

In one embodiment of the present invention, the quality estimation apparatus according to the present invention comprises a detecting (or sensing) device for detecting a temperature of a sample of a lead-free solder material and a temperature of a reference material to generate electrical signals corresponding to the detected temperatures while the sample of the lead-free solder material and the reference material are heated (and then cooled when it is optionally necessary) under the same condition, and a control device for controlling the detecting device such that the sample of the lead-free solder material and the reference material are heated (or located) as predetermined (e.g. according to a predetermined temperature profile such as a certain temperature increase and decrease rate), and for obtaining a differential thermal analysis curve of the sample of the lead-free solder material relatively to the reference material based on the electrical signals. The sensing devise is also referred to as a sensor.

As the sensor which can be used in the present invention any suitable sensors (or a measuring devise or a sensing or detecting head) can be used as far as it detect the temperature and generates the electric signals while controlling a thermal atmosphere (or a thermal condition) so as to heat and optionally cool the sample and the reference. For example, it is possible to use a sensor which comprises a furnace heated or surrounded by a temperature-controllable heater (s), two cells (or containers) located in the furnace under thermally the same condition (i.e. such that the sample and the reference are heated and optionally cooled under the same condition), thermocouples for detecting temperatures of the sample and the reference material which are located in the cells individually and for generating the electrical signals corresponding to the temperatures. This sensor may further comprise an additional thermocouple for detecting a temperature of the thermal atmosphere in the furnace and generating an electrical signal corresponding to this temperature. The same condition in the present specification means that the sample and the reference are located in a thermal atmosphere in the same manner as used in the well-known differential thermal analysis method mentioned in the above. The temperature of the thermal atmosphere is changed and preferably gradually changed so that the temperature of the reference readily follows the temperature of the thermal atmosphere. In other words, "the sample and the reference material are heated under the same condition" means that the sample is subjected to the well-known differential thermal analysis method using the reference material.

When a surrounding around the sample of the lead-free solder material is used as the reference material, the sensor detects the temperatures of the sample and the surrounding around it and generates the electric signals corresponding to these temperatures respectively while controlling the thermal atmosphere so as to heat and optionally cool the sample and the reference. The temperature of the surrounding around the sample is substantially represented by the temperature of the furnace, for example, a temperature of an atmosphere in the furnace or a body which surrounds the cell for the sample.

On the other hand, the control device which is also referred to as a controller preferably comprises a processor which has a function for processing data of the differential thermal analysis curve to obtain the characteristic value of the phase change of the sample of the lead-free solder material based on the electric signals. The controller, more specifically, may comprise a measurement unit(s) for receiving the electrical signals which are generated by the sensor and correspond to the temperatures of the sample and of the reference material respectively, an A/D converter for digitizing the electrical signals received by the measurement unit to obtain digital data of the temperatures of the sample and the reference material, and a processor (or data-processing means) which records the data of the temperatures with time to obtain data of temperature curves (or temperature change curves with time) of the sample and of the reference material and processes these data (for example, by subtracting the data of the temperature curve of the reference material from corresponding data of the temperature curve of the sample to obtain the differential thermal analysis curve, and, if necessary, by subjecting data of the differential thermal analysis curve to a suitable operation (or calculation) to obtain the characteristic values of the phase change of the sample).

Additionally, the quality estimation apparatus of the present invention further comprises a display unit for visually displaying thus obtained characteristic value of the phase change of the sample of the lead-free solder material, for example, in the form of a numerical value.

In a preferable embodiment, the processor as described above further has a function for processing and/or comparing the characteristic value of the phase change of the sample of the lead-free solder material with a predetermined threshold value to obtain a comparative result between these values. It is noted that explanations with respect to the comparative result and the threshold value have already been described in the above.

In one embodiment, a quality estimation apparatus of the present invention further comprises an alarm unit, such as a lamp, a buzzer or a display, for visually or auditorily indicating an alarm depending on the comparative result as described above so as to inform an operator that the solder material has an insufficient quality. Such alarm unit can be integrated with the display unit for visually displaying the characteristic value of the phase change as described above, however they can be separate.

In addition to, or in place of the above, the quality estimation apparatus of the present invention can be constituted such that the comparative result is withdrawn from the apparatus as an electrical signal. For instance, the comparative result as the electrical signal is transmitted to a control devise which controls a flow soldering apparatus, and this control devise controls the flow soldering apparatus based on the signal so as to renew at least a part of the solder material in a solder bath of the flow soldering apparatus for keeping the quality of the solder material sufficiently and/or to stop the operation of the flow soldering apparatus.

The quality estimating apparatus of the present invention can be used for the estimating the solder material in the solder bath of not only a single flow soldering apparatus but also a plurality of the flow soldering apparatus. Furthermore, the apparatus of the present invention can automatically estimate the quality of the solder material(s) through an on-line system when the solder material in the solder bath of one or each flow soldering apparatus is pumped up and transferred to the apparatus.

In a further aspect of the present invention, there is provided a flow soldering process using a lead-free solder material, which process comprises obtaining a sample of the lead-free solder material in a solder bath of a flow soldering apparatus and obtaining a differential thermal analysis curve of the sample relatively to a reference material by utilizing a differential thermal analysis method to estimate a quality of the lead-free solder material based on the differential thermal analysis curve.

Such flow soldering process can be constructed by combining the quality estimating method of the present invention as described above with a flow soldering process. It is noted that the explanations including the advantages as to the quality estimation method and/or the apparatus therefor as described above are also applicable to the flow soldering process as well as a flow soldering system which will be described below.

In a still further aspect of the present invention, there is provided a flow soldering system using a lead-free solder material, which system comprises a flow soldering apparatus including a solder bath which contains a lead-free solder material, and a quality estimation apparatus for estimating a quality of the lead-free solder material, wherein the quality of the lead-free solder material in the solder bath is estimated based on the differential thermal analysis curve of a sample of the lead-free solder material relative to a reference material obtained by the differential thermal analysis method.

It is desirable to use the quality estimating apparatus of the present invention as said apparatus for estimating a quality of the lead-free solder material which is included in the flow soldering process of the present invention. However, the present invention is not limited to this embodiment but can also comprise a known differential thermal analysis apparatus.

This flow soldering system can be used suitably to conduct the flow soldering process and the quality estimation method of the present invention described above. It is noted that the flow soldering apparatus and the quality estimation apparatus can be provided to the flow soldering system of the present invention in any manner as long as they are used in combination. For example, the flow soldering apparatus and the quality estimation apparatus can be combined such that they form an integrated configuration, or that they are electrically connected to each other while each of them has a separate configuration, or that they are set independently without any electrical connection between them and an operator uses them in combination.

One embodiment of the flow soldering system of the present invention can comprise one quality estimation apparatus and a plurality of the flow soldering apparatuses. In the embodiment, the quality of the solder material in the solder bath of each flow soldering apparatus is estimated using the single quality estimation apparatus. Additionally, when the system is constituted such that a sample of the solder material in the solder bath of the flow soldering apparatus is delivered to the quality estimation apparatus using a pump, the quality of the solder material can be estimated automatically and on-line.

Embodiments of the Invention

Figure 2:
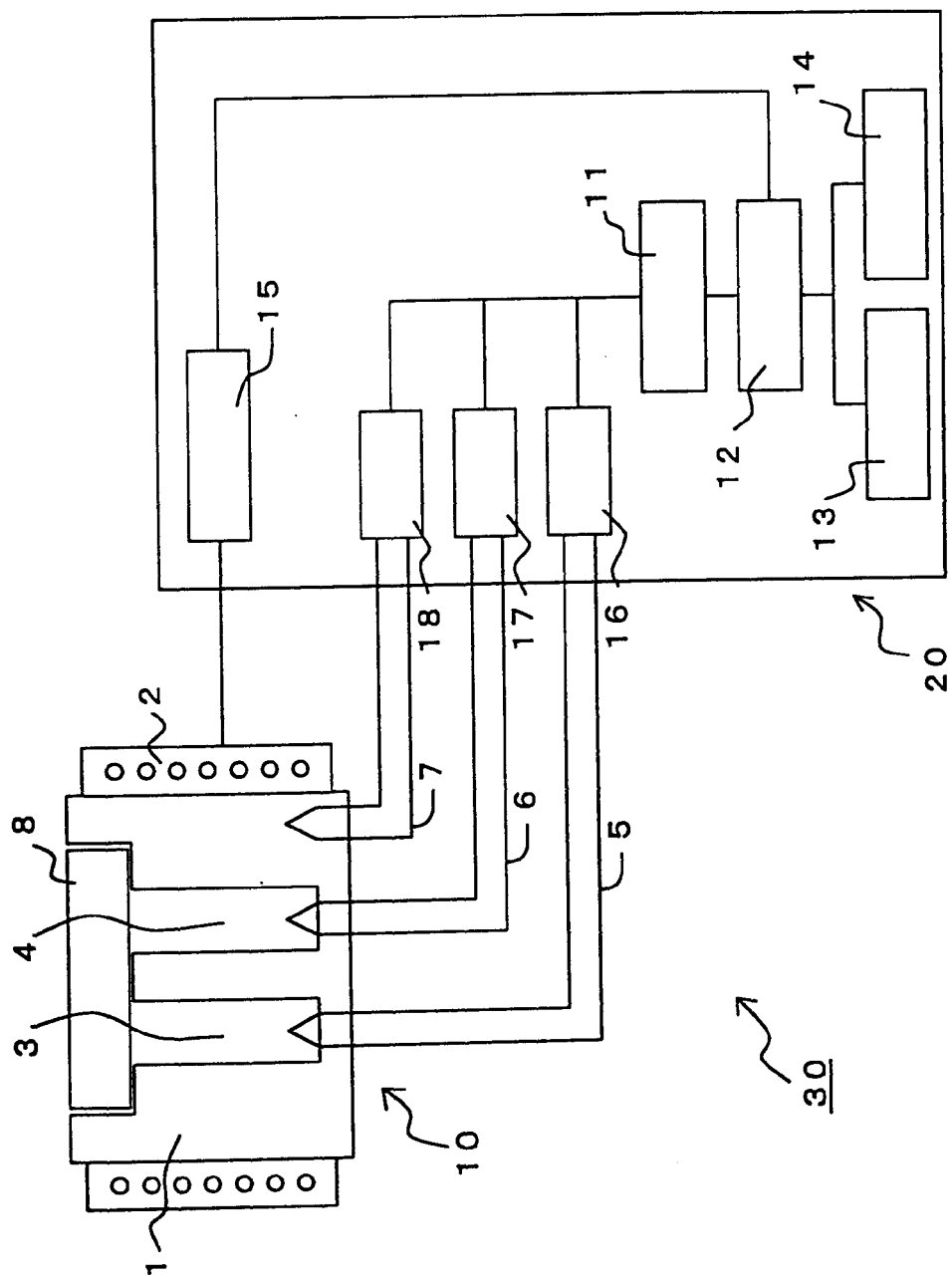
FIG. 2 shows a schematic diagram of a quality estimation apparatus in one embodiment of the present invention.
Figure 3:
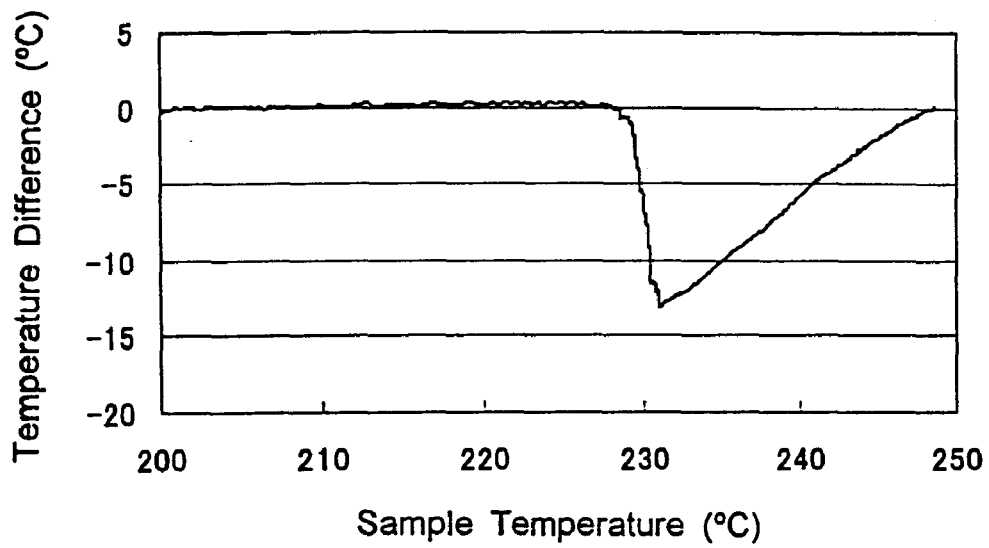
FIG. 3 is a graph which shows a part of a differential thermal analysis curve of a solder material in an example of the present invention, which includes no added Pb.
Figure 4:
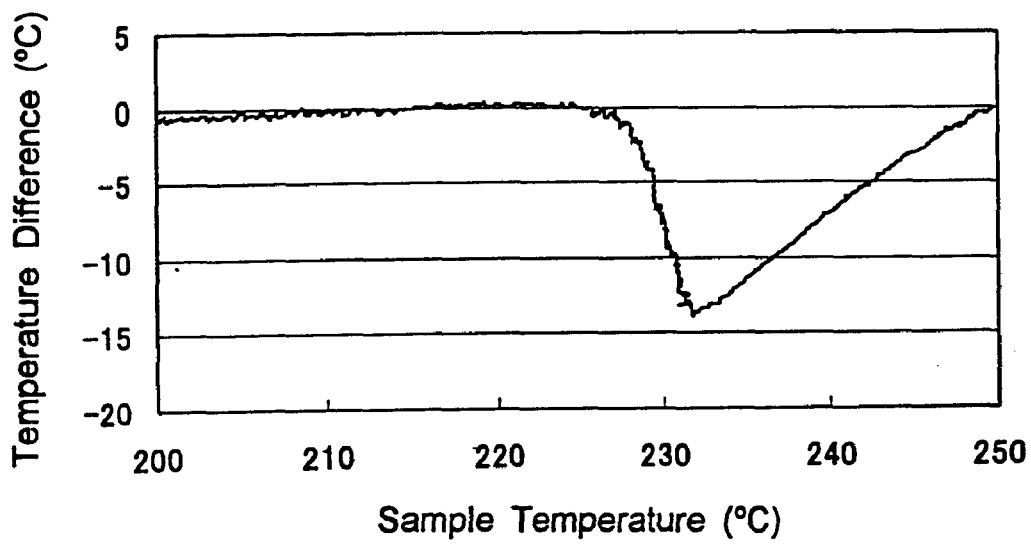
FIG. 4 is a graph which shows a part of differential thermal analysis curve of a solder material in an example of the present invention, which includes 0.1% by weight Pb.
Figure 5:
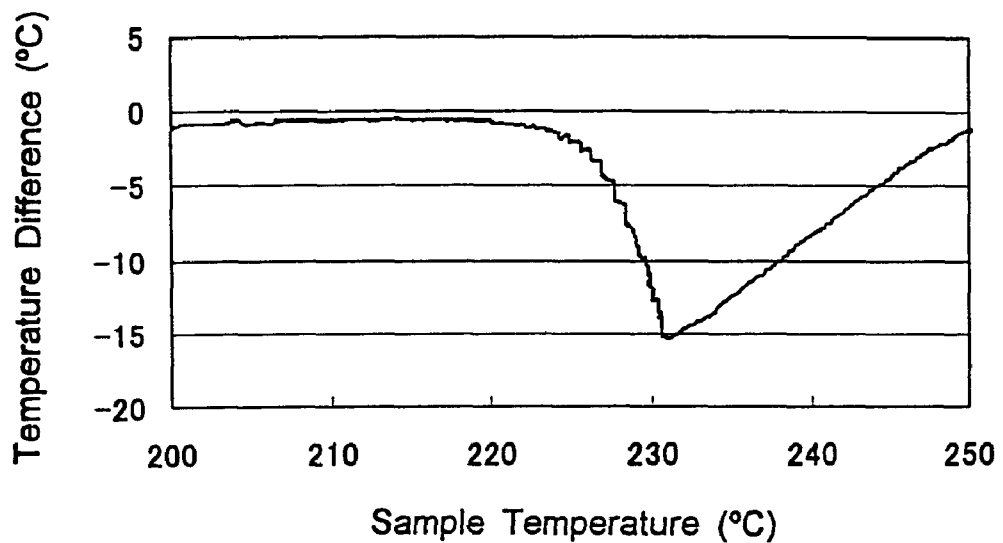
FIG. 5 is a graph which shows a part of differential thermal analysis curve of a solder material in an example of the present invention, which includes 0.3% by weight Pb.
Figure 6:
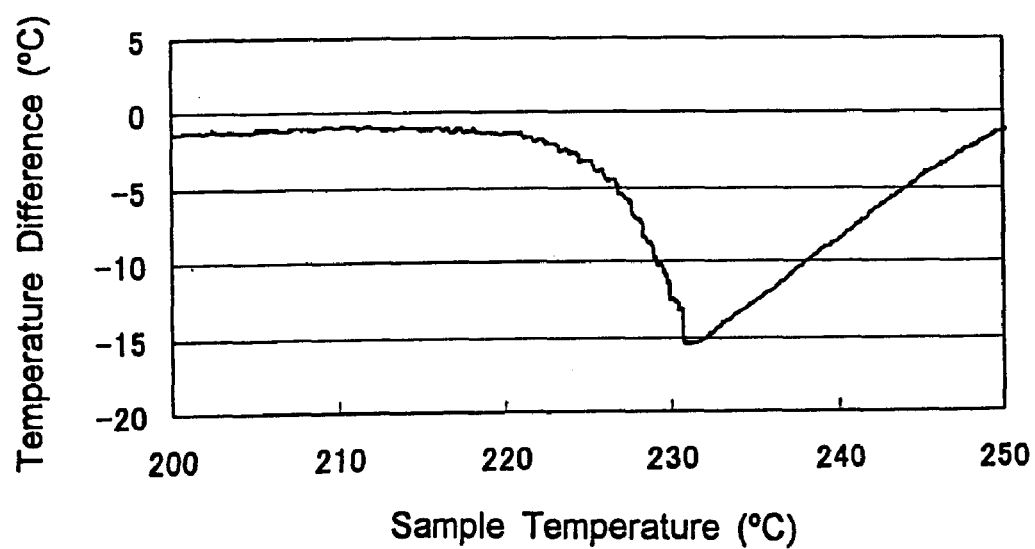
FIG. 6 is a graph which shows a part of differential thermal analysis curve of a solder material in an example of the present invention, which includes 0.5% by weight Pb.

Hereinafter, one embodiment of the present invention will be described referring to the accompanied drawings. FIG. 2 shows a schematic diagram of the quality estimation apparatus of the present embodiment.

As shown in FIG. 2, the quality estimation apparatus 30 of the present embodiment comprises a sensor (i.e. a detecting device) 10 and a control device 20. The sensor 10 functions to measure a temperature of a sample of the solder material and a temperature of a reference material, and more particularly to generate electrical signals corresponding these temperatures in the form of data, respectively. In this embodiment, the sensor 10 comprises a furnace 1; a heater 2 which is controlled with the control device 20 and is located so as to surround the furnace 1; two cells 3 and 4 which are located in the furnace 1 so as to heat and optionally cools the sample and the reference set in the cells under the same condition; thermocouples 5, 6 and 7 for individually measuring (or detecting) a temperature of the solder material (not shown), a temperature of the reference material (not shown) and a temperature of inside of the furnace 1; and a lid 8 for covering the cells 3 and 4. The thermocouples 5, 6 and 7 are respectively connected to measurement units 16 to 18 all of which are contained in the control device 20. The sensor 10 preferably has a construction such that an amount of molten Sn is fed into the cell 3 containing the sample of the solder material after the quality estimation of the sample, and then the cell automatically upsets to pour the sample and the fed material of Sn therefrom, whereby the cell is cleaned.

On the other hand, the control device 20 controls the sensor 10 and obtain a differential thermal analysis curve of the sample of the solder material relatively to the reference material based on the electrical signals generated in the sensor 10. In the present embodiment, the control device 20 is provided with a heater controller 15 for controlling the heater 2 of the sensor 10; measurement units 16, 17 and 18 for taking out the electrical signals from the sensor 10; an A/D converter 11 for digitizing the electrical signals which are taken out by using measurement units 16 to 18 and correspond to the temperatures of the sample of the solder material, the reference material and the inside of the furnace 1 respectively; a processor 12 to which the digitized signals (i.e. digital data) of the respective temperatures of the sample of the solder material, the reference material and the inside of the furnace 1 obtained by the A/D converter are transferred; an input unit 13 for inputting data to the processor 12 from the outside; and a display unit 14 for displaying results which are provided by the processor 12. The processor 12 comprises a storage means (not shown) for storing the data and a data-processing means for processing the data by arithmetic operations (not shown) as well as a control means (not shown) for controlling these means, the input unit 13, the display unit 14, and the heater controller 15. The heater controller 15 is used for controlling the heater 2 of the sensor 10 and controlled by the processor 12 with a feedback control system based on the temperature of the inside of the furnace 1 measured by the thermocouple 8 in order that the temperature of the inside of the furnace 1 is as desired. Of course, the input unit 13 and the display part 14 can also be located separately from the control device 20. As the input unit 13 and the display unit 14, any suitable unit can be used. For example, a ten key, a keyboard, or a mouse can be used as the input unit 13, and a CRT or a liquid crystal display panel which can display numeral can be used as the display unit 14.

The quality estimation apparatus 30 of the present embodiment as shown in FIG. 2 can be combined with a flow soldering apparatus (not shown) comprising a solder bath in which a solder material is supplied, so that it can possible to constitute a flow soldering system. In this system, the quality estimation apparatus 30 and the flow soldering apparatus are preferably combined such that a sample of the solder material is automatically delivered from the solder bath of the flow soldering apparatus to the quality estimation apparatus so as to estimate the sample by means of the quality estimation apparatus, and the flow soldering apparatus is automatically controlled with a feedback control operation based on the results of such estimation if necessary. However, the present invention is not limited to this embodiment, and the quality estimation apparatus 30 and the flow soldering apparatus can be arranged in respective configurations and separated by a certain distance from each other.

Hereinafter, the quality estimation method and the flow soldering process will be explained, which are conducted by using the flow soldering system as described above wherein the quality estimation apparatus 30 is combined with the flow soldering apparatus.

First, a sample of the solder material is taken out from the solder bath of the flow soldering apparatus, and delivered to the cell 3 of the sensor 10, preferably by automatically pumping. On the other hand, a reference material is set in the cell 4. As the reference material, a solder material having a predetermined composition (or an initial composition of the solder material which is supplied to the flow soldering apparatus) can be used in preference, but any suitable material such as alumina can also be used. Examples of the solder material having the predetermined composition include a solder material containing 0.5 to 1.0% by weight of Cu and the balance of Sn, a solder material containing 0.5 to 1.0% by weight of Cu, 0 to 0.5% by weight (excluding zero %) of Ag and the balance of Sn, and a solder material containing 2.5 to 4.0% by weight of Ag, 0.5 to 1.0% by weight of Cu and the balance of Sn.

Next, the quality estimation apparatus 30 is operated and the furnace 1 is heated using the heater 2 by controlling with the heater controller 15. During this stage, the temperature of the furnace 1 is measured using the thermocouple 71 and data of the temperature obtained as an electric signal via the measurement unit 18 are digitized by the A/D converter 11 and then sent to and stored in the processor 12. The processor 12 controls the heater controller 15 with the feedback control system based on the data of the temperature of the furnace 1 in order that the temperature of the furnace 1 changes (i.e. increase and/or decrease) as desired and the temperature of the reference material follows the temperature of the furnace 1. Thus, it is possible to control the temperature inside the furnace 1 appropriately.

The temperatures of the sample and the reference material are measured respectively using the thermocouples 5 and 6 while the temperature of the furnace 1 is increased and subsequently cooled at a substantially constant rate by controlling the temperature of the furnace 1 as described above. The data of the temperatures of the sample and of the reference material are obtained as the electric signals by the measurement units 16 and 17 respectively, and they are digitized by the A/D converter 11 through a procedure similar to that for digitizing the temperature of the furnace 1 as described above, and the digitized data are sent to the processor 12 to be recorded. Data of temperature curves of the sample and of the reference material are obtained by measuring and recording the temperatures of the sample and the reference material as described with the passage of time. Further, data of a differential thermal analysis curve regarding the a sample can be obtained by processing the data of these temperature curves such that the data of the temperature curve of the reference material are deducted from the data of the temperature curve of the sample corresponding to those of the reference material (or by subtracting a datum of the temperature of the reference material from that of the sample which is measured under the same condition, and repeating this subtraction for a period of the temperature measurement).

Furthermore, the characteristic value of the phase change of the sample can be obtained by processing the data of the temperature curves of the sample and the reference material, or by directly processing the data of the differential thermal analysis curve of the sample, according to a predetermined calculation procedure.

It is preferred that the display unit 14 visually displays the temperature curves of the sample and the reference material (or the data thereof), the differential thermal analysis curve of the sample (or the data thereof), and/or the characteristic value of the phase change of the sample, as described.

Then, a comparative result is obtained by comparing the characteristic value of the phase change of the sample with a predetermined threshold value. Such threshold value is determined beforehand according to a procedure which is similar to the above described procedure for obtaining the characteristic value of the sample, based on a characteristic value(s) of the phase change of a material which is made by, for example, adding at least one element selected from the group consisting of Cu, Pb, Ag, Bi and Zn to the lead-free solder material having a predetermined composition. The threshold value is preferably recorded or stored in the processor 12 by means of the input unit 13 prior to the quality estimation of the sample.

It is possible to readily estimate the quality of the sample based on the comparative result as described above. In the case where the comparative result exceeds the threshold value, it means that the quality of the solder material is not enough and the reliability characteristics of an electronic circuit board manufactured using this solder material may falls remarkably with a high possibility. In this case, a lamp (or an alarm unit) located at any suitable place such as somewhere about or on the quality estimation apparatus 30 or the flow soldering apparatus is turned on to give a caution to an operator. Alternatively, the flow soldering apparatus can be automatically controlled to renew at least a part of the solder material in the solder bath of the flow soldering apparatus and/or to stop the operation of the flow soldering apparatus.

After the measurement of the one sample of the solder material, it is preferable that a molten tin metal is supplied into the cell 3 in which the sample of the solder material has been placed, and then the cell 3 automatically upsets to pour out a mixture of the sample and the tin metal into, for example, a waste container. In this way, the cell for the sample is cleaned, so that it is suitable to obtain a solder material sample from a solder bath and estimate its quality automatically one after another and suitable, for example, for periodical estimation of the solder material.

As a result, it is possible to estimate the quality of the lead-free solder material used for flow soldering with ease by the quality estimation apparatus, the quality estimation method, the flow soldering process, and/or the flow soldering system of the present embodiment. According to the quality estimation method and apparatus, it is possible to estimate the quality of the solder material by simple operations in a short period, for example, in less than one hour, preferably in less than thirty minutes. The quality estimation apparatus has the advantage of a more compact size and a lower price compared with a conventional analyzing instrument. As a result, these advantages can also be achieved by the flow soldering process conducted by using such quality estimation apparatus and/or such quality estimation method, as well as the flow soldering system comprising such quality estimation apparatus.

Although the present invention has been explained as above with reference to one embodiment, it will be understood by those skilled in the art that the present invention is not limited to such embodiment and can be modified in various ways.

EXAMPLES

We obtained a differential thermal analysis curve of a solder material according to the quality estimation method using the quality estimation apparatus as described in the embodiment of the present invention for confirming whether the differential thermal analysis curve changes depending on an amount of addition of an additional component to the solder material. As the quality estimation apparatus used for this example, an apparatus as shown in FIG. 2 was prepared beforehand.

In this example, a model was assumed wherein Pb is mixed into a solder material of Sn-0.7Cu (i.e. a solder material consisting of 99.3% by weight of Sn and 0.7% by weight of Cu; it is noted that such expression regarding a composition of the solder material is also used hereinafter). As the following various samples were prepared and used to obtain the differential thermal analysis curve of each sample: a sample having a composition of Sn-0.7Cu (i.e. an initial sample with no addition) and samples which were prepared by adding Pb on a ratio of 0.1, 0.3, and 0.5% by weight based on the total weight to the solder material of Sn-0.7Cu respectively. Each sample had a weight in a range of about 10 to 15 g. As the reference material, Fe having almost the same volume as that of the sample was used. Temperatures of the sample and the reference material were measured while the sample and the reference material were heated under the same condition with a temperature increasing rate of about 3 to 20° C./min. in a temperature range for the measurement and thereafter cooled by a cooling fan, so that a differential thermal analysis curve of the sample relatively to the reference material was obtained. According to the above procedure, the differential thermal analysis curves were obtained for the respective samples. It is noted that Pb is a low melting point component with respect to the composition of Sn-0.7Cu.

FIGS. 3 to 6 shows differential thermal analysis curves obtained as to the various samples as described above. From FIGS. 3 to 6, it is understood that a peak of a differential thermal analysis curve became less steep, and a solidus point (i.e. a temperature where Temperature Difference separates from zero and begins to be negative) shifted toward a lower temperature side as the amount of addition of Pb was increased. In detail, although the solidus point was about 227° C. in the case of no addition (FIG. 3), it changed to about 226° C. in the case of 0.1% by weight addition (FIG. 4), about 223° C. in the case of 0.3% by weight addition (FIG. 5), and about 220° C. in the case of 0.5% by weight addition (FIG. 6), namely, the solidus point shifted toward the lower temperature side as the amount of Pb addition was increased.

It is understood that when the solidus point is selected as a characteristic value of the phase change based on such shift of the solidus point in the case where Pb is possibly mixed into the solder material of Sn-0.7Cu, one can expect a mixed ratio of Pb according to the characteristic value of a phase change of a sample of the solder material, so that the quality of the solder material ca be estimated according to a comparative result of this characteristic value of the phase change with a predetermined threshold value.

Therefore, it is understood that the quality of the solder material can be estimated based on the change in the differential thermal analysis curve of the solder material.

What is claimed is:

1. A method for detecting existence of an impurity in a lead-free solder material while conducting a flow soldering process with the lead-free solder material, which method comprises obtaining a differential thermal analysis curve of a sample of the lead-free solder material relative to a reference material by utilizing a differential thermal analysis method.

2. The method according to claim 1, which further comprises obtaining a characteristic value of a phase change of the sample of the lead-free solder material based on the differential thermal analysis curve.

3. The method according to claim 2, which further comprises displaying the characteristic value of the phase change of the sample of the lead-free solder material.

4. The method according to claim 2, which further comprises comparing the characteristic value of the phase change of the sample of the lead-free solder material with a predetermined threshold value so as to obtain a comparative result.

5. The method according to claim 4, which further comprises providing an alarm depending on the comparative result.

6. The method according to claim 4, wherein the threshold value is predetermined based on a characteristic value of a phase change of a solder material which is made by addition of at least one element selected from the group consisting of Cu, Pb, Ag, Bi and Zn to a lead-free solder material having a predetermined composition.

7. The method according to claim 6, wherein the lead-free solder material having the predetermined composition is selected from the group consisting of:

a solder material containing 0.5 to 1.0% by weight of Cu and the balance of Sn;

a solder material containing 0.5 to 1.0% by weight of Cu, greater than 0 up to 0.5% by weight of Ag and the balance of Sn; and a solder material containing 2.5 to 4.0% by weight of Ag, 0.5 to 1.0% by weight of Cu and the balance of Sn.

8. The method according to claim 7, wherein the differential thermal analysis curve is obtained by using, as the reference material, the lead-free solder material having the predetermined composition.

9. The method according to claim 1, wherein the differential thermal analysis curve is obtained by using, as the reference material, a surrounding around the sample of the lead-free solder material.

10. A process for flow soldering using a lead-free solder material, which process comprises:

obtaining a sample of the lead-free solder material in a solder bath of a flow soldering apparatus; and obtaining a differential thermal analysis curve of the sample of the lead-free solder material relative to a reference material by utilizing a differential thermal analysis method, and thereby estimating a quality of the lead-free solder material based on the differential thermal analysis curve.

11. The process according to claim 10, which further comprises obtaining a characteristic value of a phase change of the sample of the lead-free solder material based on the differential thermal analysis curve, and thereby estimating the quality of the lead-free solder material by using the characteristic value of the phase change.

12. The process according to claim 11, which further comprises displaying the characteristic value of the phase change of the sample of the lead-free solder material.

13. The process according to claim 11, which further comprises comparing the characteristic value of the phase change of the sample of the lead-free solder material with a predetermined threshold value so as to obtain a comparative result.

14. The process according to claim 13, which further comprises providing an alarm depending on the comparative result.

15. The process according to claim 13, which further comprises controlling the flow soldering apparatus depending on the comparative result to renew at least a part of the lead-free solder material in the solder bath of the flow soldering apparatus and/or to stop an operation of the flow soldering apparatus.

16. The process according to claim 13, wherein the threshold value is predetermined based on a characteristic value of a phase change of a solder material which is made by addition of at least one element selected from the group consisting of Cu, Pb, Ag, Bi and Zn to a lead-free solder material having a predetermined composition.

17. The process according to claim 16, wherein the lead-free solder material having the predetermined composition is selected from the group consisting of:
- a solder material containing 0.5 to 1.0% by weight of Cu and the balance of Sn;
- a solder material containing 0.5 to 1.0% weight of Cu, greater than 0 up to 0.5% by weight of Ag and the balance of Sn; and
- a solder material containing 2.5 to 4.0% by weight of Ag, 0.5 to 1.0% by weight of Cu and the balance of Sn.

18. The process according to claim 17, wherein the differential thermal analysis curve is obtained by using, as the reference material, the lead-free solder material having the predetermined composition.

19. The process according to claim 10, wherein the differential thermal analysis curve is obtained by using, as the reference material, a surrounding around the sample of the lead-free solder material.

* * * * *